United States Patent
Louis et al.

(10) Patent No.: US 11,420,920 B2
(45) Date of Patent: Aug. 23, 2022

(54) METHOD FOR DECREASING THE CONCENTRATION OF A METAL IN A MONOMER COMPOSITION COMPRISING BIS(BENZOYL)BENZENE

(71) Applicant: SOLVAY SPECIALTY POLYMERS USA, LLC, Alpharetta, GA (US)

(72) Inventors: Chantal Louis, Alpharetta, GA (US); Scott A. Harding, Alpharetta, GA (US)

(73) Assignee: SOLVAY SPECIALTY POLYMERS USA, LLC, Alpharetta, GA (US)

(*) Notice: Subject to any disclaimer, the term of this patent is extended or adjusted under 35 U.S.C. 154(b) by 494 days.

(21) Appl. No.: 16/471,522

(22) PCT Filed: Dec. 19, 2017

(86) PCT No.: PCT/EP2017/083673
§ 371 (c)(1),
(2) Date: Jun. 19, 2019

(87) PCT Pub. No.: WO2018/115034
PCT Pub. Date: Jun. 28, 2018

(65) Prior Publication Data
US 2019/0322609 A1    Oct. 24, 2019

Related U.S. Application Data

(60) Provisional application No. 62/437,311, filed on Dec. 21, 2016, provisional application No. 62/456,930, filed on Feb. 9, 2017.

(30) Foreign Application Priority Data

May 3, 2017    (EP) ..................... 17169169

(51) Int. Cl.
| | | |
|---|---|---|
| C07C 45/81 | (2006.01) | |
| C07C 49/00 | (2006.01) | |
| C08G 65/00 | (2006.01) | |
| C07C 49/303 | (2006.01) | |
| C08G 65/38 | (2006.01) | |

(52) U.S. Cl.
CPC ............ *C07C 45/81* (2013.01); *C07C 49/303* (2013.01); *C08G 65/38* (2013.01); *C07C 2601/16* (2017.05)

(58) Field of Classification Search
CPC ........ C07C 45/81; C07C 49/303; C08G 65/38
See application file for complete search history.

(56) References Cited

U.S. PATENT DOCUMENTS

| | | | | |
|---|---|---|---|---|
| 4,837,284 A | * | 6/1989 | Matzner | C08G 61/127 525/437 |
| 4,861,915 A | * | 8/1989 | Glendinning | C08G 65/4012 568/328 |
| 4,891,167 A | * | 1/1990 | Glendinning | C08G 65/4012 528/125 |
| 4,898,983 A | * | 2/1990 | Towle | C07C 49/813 568/322 |
| 5,250,738 A | | 10/1993 | Hackenbruch et al. | |
| 5,300,693 A | | 4/1994 | Gilb et al. | |

FOREIGN PATENT DOCUMENTS

| | | |
|---|---|---|
| CN | 1951894 A | 4/2007 |
| CN | 1974631 A | 6/2007 |
| CN | 104326895 A | 2/2015 |
| EP | 262919 A2 | 4/1988 |

OTHER PUBLICATIONS

Murphy J., in "Additives for Plastics Handbook", 2nd Edition, 2001, Chapter 5.2.3., p. 43-48—Elsevier Advanced Technology.
Blicke F.F. et al., "The Action of Aluminium Chloride on the Diphenyl Ester of Isophthalic, Terephthalic and Naphthalic Acids", J. Am. Chem. Soc., vol. 60, Oct. 8, 1938 (Oct. 8, 1938), pp. 2283-2285, XP002779749.

* cited by examiner

*Primary Examiner* — Sikarl A Witherspoon
(74) *Attorney, Agent, or Firm* — Osha Bergman Watanabe & Burton LLP

(57) ABSTRACT

Disclosed are methods of decreasing the concentration of a metal in a monomer composition including a bis(benzoyl) benzene, bis(benzoyl)benzene monomer compositions having a low total metal concentration, di-ketone polymers made from low metal bis(benzoyl)benzene monomers, and polymer compositions and shaped articles including the di-ketone polymers. It was surprisingly found that di-ketone polymers made by nucleophilic substitution of low metal bis(benzoyl)benzene monomers exhibit greater crystallinity, as compared with di-ketone polymers made with conventional monomers.

17 Claims, No Drawings

METHOD FOR DECREASING THE CONCENTRATION OF A METAL IN A MONOMER COMPOSITION COMPRISING BIS(BENZOYL)BENZENE

CROSS-REFERENCE TO RELATED APPLICATIONS

This application claims priority to U.S. Provisional Application No. 62/437,311 filed Dec. 21, 2016, U.S. Provisional Application No. 62/456,930 filed Feb. 9, 2017, and European Application No. EP 17169169.4 filed May 3, 2017, the whole content of these applications being incorporated herein by reference for all purposes.

FIELD OF THE INVENTION

The present invention relates to a method of decreasing the concentration of a metal in a bis(benzoyl)benzene monomer composition, bis(benzoyl)benzene monomer compositions having a low total metal concentration, di-ketone polymers made from low metal monomers, and polymer compositions and shaped articles including the di-ketone polymers.

BACKGROUND

Poly(aryl ether ketone) (PAEK) polymers including bis(benzoyl)benzene moieties ("di-ketone polymers"), commonly formulated as composites including reinforcing fillers, are well-suited for use in a variety of demanding application settings including, but not limited to, aerospace and oil and gas drilling, where high crystallinity and excellent chemical resistance is of great importance; however, an ongoing need exists for di-ketone polymers with improved crystallinity and chemical resistance without significantly impacting the processability and mechanical properties of the polymers.

DETAILED DESCRIPTION OF THE INVENTION

Described herein are methods of decreasing the concentration of a metal in a monomer composition including a bis(benzoyl)benzene, bis(benzoyl)benzene monomer compositions having a low total metal concentration, di-ketone polymers made from low metal bis(benzoyl)benzene monomers, and polymer compositions and shaped articles including the di-ketone polymers.

Applicants surprisingly found that di-ketone polymers made by a nucleophilic substitution from low metal bis(benzoyl)benzene monomers exhibit greater crystallinity as compared with di-ketone polymers made with conventional monomers ("traditional di-ketone polymers").

For clarity, the term "low metal monomer" means a monomer composition having a total metal concentration of less than 30 parts per million by weight (wt.ppm), preferably less than 25 wt.ppm, relative to the weight of the monomer composition. The term "metal," as used herein means aluminum, iron, sodium, potassium, or calcium, including elemental metal, metal ions, metal salts, and metal oxides thereof. The term "total metal concentration," means the sum of the concentrations of aluminum, iron, sodium, potassium, and calcium as determined by elemental analysis, as described in the examples below.

Traditionally, bis(benzoyl)benzene monomers are recrystallized using recrystallization solvents with relatively low polarity (e.g., solvents with a dielectric constant ($\varepsilon$)≤30). It was generally thought that use of high polarity solvents would lead to low recrystallization yields—even at low temperatures—because of the increased solubility of bis(benzoyl)benzene monomers and the concomitant decrease in solvent selectivity between the bis(benzoyl) benzene monomers and impurities.

Nevertheless, Applicants surprisingly discovered that recrystallizing a bis(benzoyl)benzene monomer composition in a first solvent (Solvent A) including 1) at least 10 wt. % of an aprotic solvent having a dielectric constant greater than 30 relative to the total weight of Solvent A and 2) less than 1 wt. % of inorganic salts relative to the total weight of Solvent A, produces both high recrystallization yields (e.g. ≥90%) and significantly reduces the concentration of metals in the monomer composition. Moreover, in some embodiments, it was also surprisingly found possible to recrystallize using monomer concentrations above 10 wt. % of monomers, thereby increasing solvent usage efficiency.

Bis(benzoyl)benzene Monomers

The bis(benzoyl)benzene monomers are selected from the group consisting of compounds of formulas (I), (II), (III), and (IV):

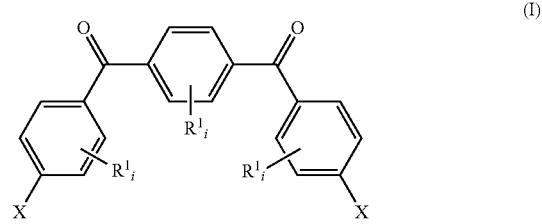

(I)

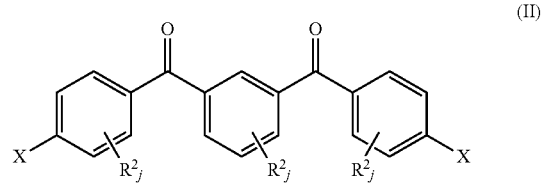

(II)

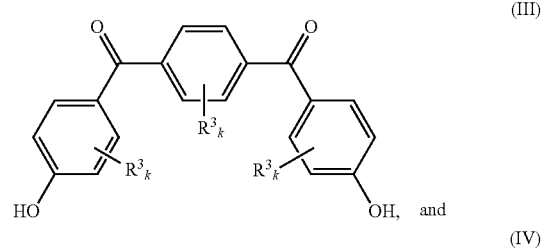

(III)

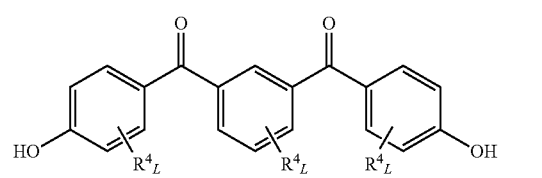

(IV)

where $R^1$, $R^2$, $R^3$ and $R^4$, at each instance, is independently selected from the group consisting of an alkyl, an alkenyl, an alkynyl, an aryl, an ether, a thioether, a carboxylic acid, an ester, an amide, an imide, an alkyl phosphonate, an amine, and a quaternary ammonium; i, j, k and L, at each instance, is an independently selected integer ranging from 0 to 4, preferably 0; and X is a halogen, preferably fluorine or chlorine, more preferably fluorine.

In some embodiments, each of i, j, k and L is zero, and X is fluorine such that the bis(benzoyl)benzene monomers are selected from the group consisting of:

1,4-bis(4'-fluorobenzoyl)benzene (1,4-DFDK),
1,3-bis(4'-fluorobenzoyl)benzene (1,3-DFDK),
1,4-bis(4'-hydroxybenzoyl)benzene (1,4-BHBB), and
1,3-bis(4'-hydroxybenzoyl)benzene (1,3-BHBB).

Preferably, the bis(benzoyl)benzene monomers are selected from the group consisting of 1,4-DFDK, 1,4-BHBB and 1,3-BHBB, more preferably 1,4-DFDK and 1,4-BHBB.

Method of Decreasing the Concentration of Metals in a Bis(benzoyl)benzene Monomer Composition As discussed above, Applicants surprisingly discovered that recrystallizing a bis(benzoyl)benzene monomer composition in Solvent A produces both high recrystallization yields (e.g. ≥90%) and significantly reduces the concentration of metals in the monomer composition.

The method includes the following general steps, which will be described in more detail below:

a) dissolving the monomer composition to form a monomer solution,
b) recrystallizing the monomer composition from the monomer solution, and
c) recovering the monomer composition from the recrystallized monomer solution.

a) Dissolution Step

Dissolving the monomer composition (referred to herein as the "dissolution step") includes dissolving the monomer composition to form a monomer solution by heating the monomer composition in Solvent A to a first temperature ($T_1$). As used herein "dissolving" means that at least 90% of the monomer composition is in solution. Preferably at least 95%, more preferably at least 99% of the monomer composition is in solution.

Solvent A includes at least 10 wt. %, preferably at least 20 wt. %, 30 wt. %, 40 wt. %, 50 wt. %, 60 wt. %, 70 wt. %, 80 wt. %, 90 wt. %, 95 wt. %, most preferably at least 99 wt. %, relative to the total weight of Solvent A, of an aprotic solvent having a dielectric constant greater than 30, preferably greater than 35, most preferably greater than or equal to 37. The aprotic solvent has a dielectric constant less than 90, preferably less than 80, more preferably less than 70. The aprotic solvent of Solvent A preferably comprises dimethyl sulfoxide (DMSO), sulfolane, propylene carbonate, N,N'-dimethylformamide (DMF), N,N'-dimethylacetamide (DMAc), N-methylpyrrolidinone (NMP), 1,3-dimethyl-2-oxo-hexahydropyrimidine (DMPU), 1,3-dimethylimidazolidin-2-one (DMEU) or a combination thereof. For dissolving of monomer compositions including the bis(benzoyl)benzene monomers of formulae (I) or (II), the aprotic solvent of Solvent A preferably comprises dimethyl sulfoxide (DMSO), sulfolane, propylene carbonate, or a combination thereof. For dissolving of monomer compositions including the bis(benzoyl)benzene monomers of formulae (III) or (IV), the aprotic solvent of Solvent A preferably comprises dimethyl sulfoxide (DMSO), sulfolane, N,N'-dimethylformamide (DMF), N,N'-dimethylacetamide (DMAc), N-methylpyrrolidinone (NMP), 1,3-dimethyl-2-oxo-hexahydropyrimidine (DMPU), 1,3-dimethylimidazolidin-2-one (DMEU), or a combination thereof.

Solvent A also includes less than 1 wt. %, preferably less than 0.5 wt. %, 0.4 wt. %, 0.3 wt. %, 0.2 wt. %, most preferably less than 0.1 wt. % of inorganic salts relative to the total weight of Solvent A. The inorganic salts preferably comprise halides or oxides of Group Ia, IIa, IIIa or VIII elements of the periodic table, such as NaF, KF, CsF, NaOH, KOH, CsOH, NaCl, KCl, CsCl, FeCl$_3$, AlCl$_3$, or a combination thereof.

The first temperature ($T_1$) ranges from about 50 to about 240° C., preferably from about 50 to about 200° C., more preferably from about 50 to about 180° C., most preferably from about 50 to about 150° C.

The dissolving of the monomer composition can be performed at atmospheric, super-atmospheric or sub-atmospheric pressure, preferably at atmospheric or super-atmospheric pressure, where "atmospheric pressure" is 101.3 kiloPascals ("kPa").

The concentration of the monomer composition in the monomer solution ranges from about 10 to about 20 wt. %, preferably from about 10 to about 15 wt. % relative to the combined weight of the monomer composition and Solvent A.

b) Recrystallization Step

Recrystallizing the monomer composition from the monomer solution (referred to herein as the "recrystallization step") includes at least one of a distillation step and a cooling step. In some embodiments, the recrystallization step can further include one or more optional steps. The recrystallization can be summarized as follows:

b1) optional filtration step ("optional first filtration")
b2) optional distillation step, ("optional distillation")
b3) optionally adding a second solvent ("optional addition of Solvent B"), and
b4) optional cooling step ("cooling").

Step b1), when present, is performed before steps b2), b3), and b4), when present. Steps b2), b3), and b4), when present, are preferably performed separately in order. Nevertheless, in some embodiments, steps b2), b3), and b4), when present, are preferably performed in order, but performance of at least two of the steps overlaps in time (e.g., performance of step b4) may start before performance of step b2) is completed). In alternative embodiments, at least two of steps b2), b3), and b4) are performed simultaneously. For example, when an adiabatic crystallizer is used, the distillation (step b2)) and the cooling (step b4)) are simultaneous.

Recrystallization sub-steps b1), b2), b3), and b4), will now be described in detail:

b1) Optional First Filtration

After the dissolving step, the method can optionally further include a first filtration, in which the monomer solution is passed through a first filter at the temperature $T_1$. Preferably, the first filter has a nominal porosity ranging from about 0.45 to about 10 µm, more preferably from about 1 to about 5 µm. The first filtration may separate portions of the monomer composition that did not dissolve in step a) (e.g. elemental metals, metal oxides, etc.) from the monomer solution.

b2) Optional Distillation

In step b2), a portion of Solvent A may optionally be distilled off at a second temperature ($T_2$). Preferably at least 20 wt. %, more preferably at least 30 wt. % of Solvent A is distilled off, relative to the total weight of the monomer solution before distillation.

The second temperature ($T_2$) may be identical to or different from the first temperature ($T_1$) and is independently selected from temperatures ranging from about 50 to about 240° C., preferably from about 50 to about 200° C., more preferably from about 50 to about 180° C., most preferably from about 50 to about 150° C.

Distillation can be performed at atmospheric, super-atmospheric or sub-atmospheric pressure, preferably at atmospheric or sub-atmospheric pressure.

The optional distillation may be performed for a time ($t_1$). Time ($t_1$) preferably ranges from 5 minutes to 720 minutes, preferably from 15 minutes to 600 minutes, more preferably from 60 minutes to 500 minutes.

In some embodiments, the distillation causes precipitation of monomer, preferably low metal monomer.

b3) Optional Addition of Solvent B

In some embodiments, a second solvent (Solvent B) that is miscible with Solvent A is added to the monomer solution to reduce the solubility of the monomer composition in the monomer solution. Reducing the solubility of the monomer composition in the monomer solution may ease precipitation of the monomer composition by promoting precipitation at higher temperatures or higher solvent volumes.

Thus, in some embodiments, a solvent mixture is formed by adding Solvent B to the monomer solution when the monomer solution is at a third temperature ($T_3$). Solvent B is preferably added to the monomer solution at a concentration ranging from about 5.0 to about 50 wt. %, preferably from about 7.0 to about 40 wt. %, more preferably from about 10 to about 30 wt. %, relative to the total weight of Solvents A and B.

Preferably, the solubility of the monomer composition in Solvent B is less than the solubility of the monomer composition in Solvent A such that the solubility of the monomer composition in the solvent mixture is less than the solubility of the monomer composition in Solvent A. In some embodiments, the addition of Solvent B results in precipitation of monomer, preferably low metal monomer. In alternative embodiments, the addition of solvent B does not result in the precipitation of the monomer composition at the temperature ($T_3$).

In some embodiments, Solvent B includes water, ethanol, methanol, isopropanol, acetone, acetic acid, acetonitrile, ethyl acetate, diethyl ether, tetrahydrofuran, dipropyl ether, or a combination thereof. Solvent B preferably includes water, ethanol, methanol or isopropanol.

The third temperature ($T_3$) may be identical to or different from the first temperature ($T_1$) or the second temperature ($T_2$), and is independently selected from a temperature ranging from about 50 to about 240° C., preferably from about 50 to about 200° C., more preferably from about 50 to about 180° C., most preferably from about 50 to about 150° C.

The addition of Solvent B can be performed at atmospheric, super-atmospheric or sub-atmospheric pressure, preferably at atmospheric or super-atmosphere pressure.

The addition of Solvent B may be performed for a time ($t_2$). Time ($t_2$) preferably ranges from 5 minutes to 720 minutes, preferably from 15 minutes to 600 minutes, more preferably from 60 minutes to 500 minutes.

b4) Cooling

In step b4), the monomer solution may optionally be cooled to a fourth temperature ($T_4$) ranging from about −10 to about 40° C., preferably from about 0 to about 15° C., provided that the fourth temperature ($T_4$) is greater than the melting point of Solvent A and of the optional Solvent B. The monomer solution may be cooled at a rate ranging from about 0.1° C./min to about 10° C./min, preferably from about 0.15° C./min to about 5° C./min, more preferably about 0.2° C./min to about 3° C./min.

In some embodiments, the cooling causes precipitation of monomer, preferably low metal monomer.

Thus, in some embodiments, the method includes the following steps in order: b1) first filtration, b3) addition of Solvent B, b4) cooling. In alternative embodiments, the method includes the following steps in order: b3) addition of Solvent B, b4) cooling. In alternative embodiments, the method includes the following steps in order: b1) first filtration, b2) distillation, b4) cooling.

c) Recovery Step

The method also includes recovering the monomer composition, preferably low metal monomer, by removing precipitated monomer composition from the monomer solution. The recovery step includes the following sub-steps:

c1) Optional second filtration c2) Optional washing c3) Drying

In the optional second filtration, the monomer solution can be passed through a second filter. Preferably, the second filter has a nominal porosity ranging from about 0.45 to about 10 µm.

Optionally, the monomer composition is washed with a third solvent (Solvent C), preferably when the monomer composition is at the fourth temperature ($T_4$). Solvent C may be identical to Solvent A, Solvent B, or a combination thereof. Solvent C is miscible in Solvent A and optional Solvent B.

Finally, the monomer composition is dried, with or without heating, and with or without vacuum to yield a low metal monomer. The yield of low metal monomer is preferably at least 90 wt. % relative to the weight of the monomer composition prior to performance of the method.

The method can be performed continuously or in batch mode. Typical industrial equipment which can be used in the method includes non-agitated or agitated cooling crystallizers, evaporating crystallizers, vacuum crystallizers, continuous crystallizers, such as forced-circulation crystallizers, fluidized-bed crystallizers, and draft-tube agitated vacuum crystallizers.

In some embodiments, the method results in a monomer composition having a total metal concentration less than 30 wt.ppm, preferably less than 25 wt.ppm, relative to the total weight of the monomer composition, as measured in the examples below.

In some embodiments, the method results in a reduction in the total metal concentration of at least 50%, preferably at least 60%.

Thus, exemplary embodiments also include a monomer composition, preferably a monomer composition recrystallized by the methods described herein, where the monomer composition has a total metal concentration less than 30 wt.ppm, preferably less than 25 wt.ppm, relative to the total weight of the monomer composition, as measured in the examples below.

Di-Ketone Polymers

As discussed above, it was surprisingly found that di-ketone polymers made via nucleophilic substitution from low metal monomers exhibit greater crystallinity as compared with di-ketone polymers made with conventional monomers.

A "di-ketone polymer" as used herein means a polymer comprising more than 50 mol % of recurring units ($R_{DK}$) selected from the group consisting of units of formulae (V) to (IX) below:

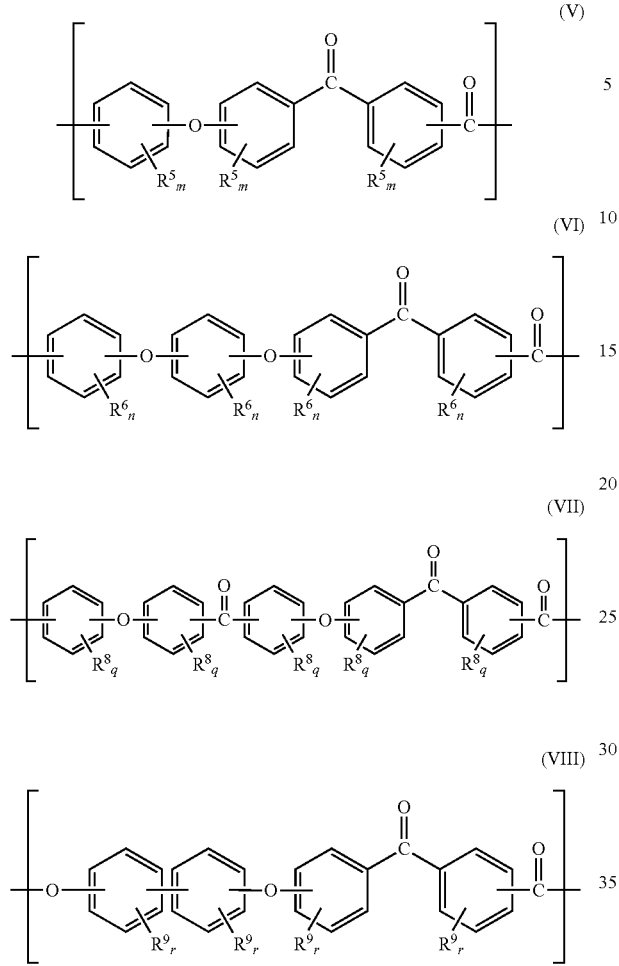

where $R^5$, $R^6$, $R^8$, and $R^9$, at each instance, is independently selected from the group consisting of an alkyl, an alkenyl, an alkynyl, an aryl, an ether, a thioether, a carboxylic acid, an ester, an amide, an imide, an alkyl sulfonate, an alkyl phosphonate, an amine, and a quaternary ammonium; and m, n, q, and r, at each instance, is an independently selected integer ranging from 0 to 4. Preferably each of m, n, q, and r is 0.

Preferably, the phenylene moieties in recurring units ($R_{DK}$) have 1,3- or 1,4-linkages.

Preferably at least 60 mol %, 70 mol %, 80 mol %, 90 mol %, 95 mol %, 99 mol % of recurring units ($R_{DK}$) are selected from the group consisting of recurring units of formulae (V), (VI), (VII), and (VIII).

In some embodiments, the di-ketone polymer is poly (ether ketone ketone) (PEKK). As used herein, a "poly(ether ketone ketone) (PEKK)" denotes any polymer of which more than 50 mol % of the recurring units ($R_{DK}$) are a combination of recurring units of formulas (V-A) and (V-B):

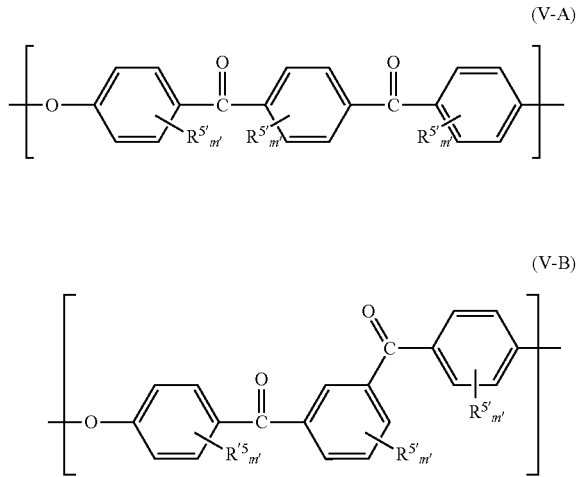

where $R^{5'}$ and m', at each instance, are independently selected from the groups described above for $R^5$ and m, respectively. Preferably each m' in formulae (V-A) and (V-B) is zero.

Preferably at least 60 mol %, 70 mol %, 80 mol %, 90 mol %, 95 mol %, 99 mol % of recurring units ($R_{DK}$) are a combination of recurring units (V-A) and (V-B).

In some embodiments, the mol ratio of units (V-A):(V-B) ranges from 50:50 to 85:15, preferably from 55:45 to 80:20, more preferably from 65:35 to 75:25.

In some embodiments, the di-ketone polymer is poly (ether ether ketone ketone) (PEEKK). As used herein, a "poly(ether ether ketone ketone) (PEEKK)" denotes any polymer of which more than 50 mol % of the recurring units ($R_{DK}$) are recurring unit of formula (VI-A):

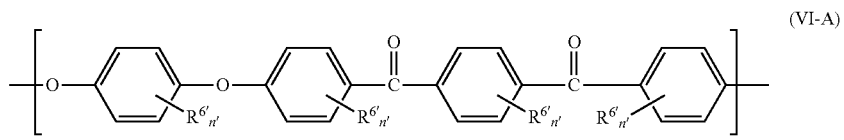

where $R^{6'}$ and n', at each instance, are independently selected from the groups described above for $R^6$ and n, respectively. Preferably each n' in formulae (VI-A) is zero.

Preferably at least 60 mol %, 70 mol %, 80 mol %, 90 mol %, 95 mol %, 99 mol % of recurring units ($R_{DK}$) are recurring units of formula (VI-A).

In some embodiments, the di-ketone polymer is poly (ether ketone ether ketone ketone) (PEKEKK). As used herein, a "poly(ether ketone ether ketone ketone) (PEKEKK)" denotes any polymer of which more than 50 mol % of the recurring units ($R_{DK}$) are recurring unit of formula (VII-A):

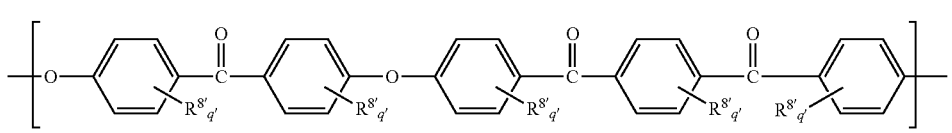

(VII-A)

where $R^{8'}$ and q', at each instance, are independently selected from the groups described above for $R^8$ and q, respectively. Preferably each q' in formulae (VII-A) is zero.

Preferably at least 60 mol %, 70 mol %, 80 mol %, 90 mol %, 95 mol %, 99 mol % of recurring units ($R_{DK}$) are recurring units of formula (VII-A).

In some embodiments, the di-ketone polymer is poly (ether diphenyl ether ketone ketone) (PEDEKK). As used herein, a "poly(ether diphenyl ether ketone ketone) (PEDEKK)" denotes any polymer of which more than 50 mol % of the recurring units ($R_{DK}$) are recurring unit of formula (VIII-A):

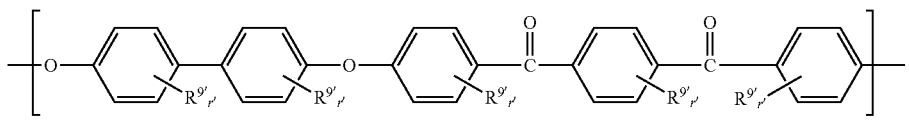

where $R^{9'}$ and r', at each instance, are independently selected from the groups described above for $R^9$ and r, respectively. Preferably each r' in formulae (VIII-A) is zero.

Preferably at least 60 mol %, 70 mol %, 80 mol %, 90 mol %, 95 mol %, 99 mol % of recurring units ($R_{DK}$) are recurring units of formula (VIII-A).

In some embodiments, the di-ketone polymer is poly (ether diphenyl ether ketone meta ketone) (PEDEKmK). As used herein, a "poly(ether diphenyl ether ketone meta ketone) (PEDEKmK)" denotes any polymer of which more than 50 mol % of the recurring units ($R_{DK}$) are recurring unit of formula (VIII-B):

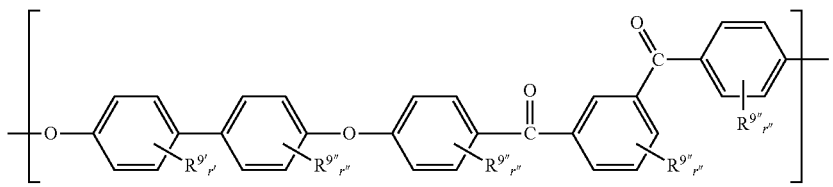

where $R^{9''}$ and r'', at each instance, are independently selected from the groups described above for $R^9$ and q, respectively. Preferably each r'' in formulae (VIII-B) is zero.

Preferably at least 60 mol %, 70 mol %, 80 mol %, 90 mol %, 95 mol %, 99 mol % of recurring units ($R_{DK}$) are recurring units of formula (VIII-B).

The di-ketone polymer is preferably PEKK, PEKEKK, or PEDEKK, preferably PEKK or PEKEKK, and most preferably PEKK.

In some embodiments, the di-ketone polymer includes at least 5, preferably at least 7, most preferably at least 10 recurring units ($R_{DK}$).

In some embodiments, the di-ketone polymer has a total aluminum and iron concentration of less than 30 wt.ppm, relative to the weight of the di-ketone polymer.

The di-ketone polymer may be synthesized from monomers including bis(benzoyl)benzene monomers, where at least 80 mol %, preferably at least 90 mol %, and most preferably at least 95 mol % of the bis(benzoyl)benzene monomers are bis(benzoyl)benzene monomers recrystallized according to the methods described herein.

The di-ketone polymer may also be synthesized from monomers including bis(benzoyl)benzene monomers, where at least 80 mol %, preferably at least 90 mol %, and most preferably at least 95 mol % of the bis(benzoyl)benzene monomers are low metal monomers.

Di-Ketone Polymer Compositions

The di-ketone polymers described herein can be used in polymer compositions and incorporated into shaped articles, including but not limited to mobile electronic devices, medical devices, and composite materials. Furthermore, the di-ketone polymers, or compositions thereof, can also be used in additive manufacturing applications.

Polymer compositions including the di-ketone polymers ("di-ketone polymer compositions") can include a reinforcing filler. Reinforcing fillers include fibrous fillers and particulate fillers, distinct from the pigments described below. Particulate filers include mineral fillers including, but not limited to, talc, mica, kaolin, calcium carbonate, calcium silicate, and magnesium carbonate. Fibrous fillers include, but are not limited to, glass fiber, carbon fiber, synthetic polymeric fiber, aramid fiber, aluminum fiber, titanium fiber, magnesium fiber, boron carbide fiber, rock wool fiber, steel fiber, wollastonite. Preferably the reinforcing filler is selected from mica, kaolin, calcium silicate, magnesium carbonate, glass fiber, carbon fiber, wollastonite, and any combination of one or more thereof.

Preferably, the filler is a fibrous filler. A particular class of fibrous fillers are whiskers, i.e. single crystal fibers made from various raw materials, such as $Al_2O_3$, SiC, BC, Fe and Ni. In one embodiment, the reinforcing filler is selected from wollastonite and glass fiber. Among fibrous fillers, glass fibers are preferred; they include chopped strand A-, E-, C-, D-, S-, T- and R-glass fibers, as described in chapter 5.2.3, p. 43-48 of Additives for Plastics Handbook, 2nd edition, John Murphy.

When the glass fibers have a circular cross-section, they may have an average glass fiber diameter of 3 to 30 µm, preferably 5 to 12 µm. Different kinds of glass fibers with a circular cross-section are available on the market depending on the type of the glass they are made of. Glass fibers made from E- or S-glass are examples.

In some embodiments, the reinforcing filler includes carbon fiber. As used herein, the term "carbon fiber" is intended to include graphitized, partially graphitized and ungraphitized carbon reinforcing fibers or a mixture thereof. Carbon fibers can advantageously be obtained by heat treatment and pyrolysis of different polymer precursors such as, for example, rayon, polyacrylonitrile (PAN), aromatic polyamide or phenolic resin; carbon fibers may also be obtained from pitchy materials. The term "graphite fiber" denotes carbon fibers obtained by high temperature pyrolysis (over 2000° C.) of carbon fibers, where the carbon atoms place in a way similar to the graphite structure. Carbon fibers are preferably selected from PAN-based carbon fibers, pitch based carbon fibers, graphite fibers, and any combination of one or more thereof.

The weight of the reinforcing filler is preferably less than 80% wt., more preferably less than 70% wt., and even more preferably less than 65% wt., based on the total weight of the composition.

In some embodiments, the di-ketone polymer compositions can include, in addition or alternatively to the reinforcing filler, one or more additional ingredients selected from the group consisting of (i) colorants (e.g. a dye); (ii) pigments (e.g., titanium dioxide, zinc sulfide and zinc oxide); (iii) light stabilizers (e.g. UV stabilizers); (iv) heat stabilizers; (v) antioxidants (e.g. organic phosphites and phosphonites); (vi) acid scavengers (vii) processing aids (viii) nucleating agents (ix) plasticizer, internal lubricants, and external lubricants; (x) flame retardants (xi) smoke-suppressing agents (x) anti-static agents (xi) anti-blocking agents (xii) conductivity additives (e.g. carbon black and carbon nanofibrils) (xiii) plasticizers; (xiv) flow modifiers; (xv) extenders; (xvi) metal deactivators and any combination of one or more thereof. In some embodiments, the total concentration of additional ingredients is less than 20%, preferably less than 10%, more preferably less than 5% and even more preferably less than 2%, based upon the total weight of the polymer composition.

In some embodiments, the composition comprises the di-ketone polymer in combination with one or more than one additional polymeric components, such as polyarylether polymers different from the di-ketone polymer, including, but not limited to, poly(ether ether ketone) ("PEEK") polymers, poly(ether ketone) ("PEK") polymers, sulfone polymers, and polyaryl sulfide polymers. According to other embodiments, the di-ketone polymer is the only polymeric component in the di-ketone polymer composition. The expression "polymeric components" is to be understood as encompassing compounds having repeated linked units and a molecular weight of 2,000 g/mol or more.

The di-ketone polymer compositions can be prepared by a variety of methods involving intimate admixing of the di-ketone polymer, optionally the reinforcing filler and optionally the above described additional ingredients desired in the di-ketone polymer composition, for example by dry blending, suspension or slurry mixing, solution mixing, melt mixing or a combination of dry blending and melt mixing.

Typically, the dry blending of di-ketone polymer, preferably in powder state, optionally the reinforcing filler and optionally additional ingredients is carried out with high intensity mixers, such as Henschel-type mixers or ribbon mixers so as to obtain a physical mixture, in particular a powder mixture of the at least one di-ketone polymer, optionally the reinforcing filler and optionally additional ingredients. Alternatively, the intimate admixing of the di-ketone polymer, optionally the reinforcing filler and optionally additional ingredients desired in the di-ketone polymer composition, is carried out by tumble blending based on a single axis or multi-axis rotating mechanism so as to obtain a physical mixture.

Alternatively, the slurry mixing of the di-ketone polymer, optionally the reinforcing filler and optionally additional ingredients is carried out by first slurrying of the di-ketone polymer in powder form, optionally the reinforcing filler and optionally additional ingredients using an agitator in an appropriate liquid such as for example methanol, followed by filtering the liquid away, so as to obtain a powder mixture of the at least one di-ketone polymer, optionally the reinforcing filler and optionally additional ingredients.

In another embodiment, the solution mixing of the di-ketone polymer, as detailed above, optionally the reinforcing filler and optionally additional ingredients using an agitator in an appropriate solvent or solvent blends such as for example diphenyl sulfone, benzophenone, 4-chlorophenol, 2-chlorophenol, meta-cresol. Diphenyl sulfone is most preferred.

Following the physical mixing step by one of the aforementioned techniques, the physical mixture, in particular, the obtained powder mixture, of the at least one di-ketone polymer, optionally the reinforcing filler and optionally additional ingredients is typically melt fabricated by known methods in the art including melt fabrication processes such as compression molding, injection molding, extrusion and the like, to provide shaped articles.

The so-obtained physical mixture, in particular the obtained powder mixture can comprise the di-ketone polymer, the reinforcing filler, as detailed above, and optionally, other ingredients in the weight ratios as above detailed, or can be a concentrated mixture to be used as masterbatch and diluted in further amounts of the di-ketone polymer, as above detailed, the reinforcing filler, as detailed above, and optionally, other ingredients in subsequent processing steps. For example, the obtained physical mixture can be extruded into a stock shape like a slab or rod from which a final part can be machined. Alternatively, the physical mixture can be compression molded into a finished part or into a stock shape from which a finished part can be machined.

It is also possible to manufacture the composition of the invention by further melt compounding the powder mixture as above described. As said, melt compounding can be effected on the powder mixture as above detailed, or directly on the di-ketone polymer, as above detailed, the reinforcing filler, as detailed above, and optionally, other ingredients. Conventional melt compounding devices, such as co-rotating and counter-rotating extruders, single screw extruders, co-kneaders, disc-pack processors and various other types of extrusion equipment can be used. Preferably, extruders, more preferably twin screw extruders can be used.

If desired, the design of the compounding screw, e.g. flight pitch and width, clearance, length as well as operating conditions will be chosen so that sufficient heat and mechanical energy is provided to advantageously fully melt the powder mixture or the ingredients as above detailed and obtain a homogeneous distribution of the different ingredients. Provided that optimum mixing is achieved between the bulk polymer and filler contents, it is advantageously possible to obtain strand extrudates of the di-ketone polymer composition of the invention. Strand extrudates of the di-ketone polymer composition can be chopped with e.g. a rotating cutting knife after some cooling time on a conveyer with water spray. Thus, for example a di-ketone polymer composition which may be present in the form of pellets or beads can then be further used for the manufacture of shaped articles of different shapes and sizes.

Shaped Articles

The di-ketone polymer compositions (or di-ketone polymer) can be incorporated into shaped articles. The shaped articles can be made from the di-ketone polymer composition using any suitable melt-processing technique including, but not limited to, extrusion molding, injection molding, and compression molding. In some embodiments, the shaped articles are in the form of bidimensional articles. Bidimensional articles include parts in which one dimension (thickness or height) is significantly less than the other two characterizing dimensions (width and length), for example, films and sheets. In some embodiments, the shaped article can be a coating. In some embodiments, the shaped articles are three-dimensional parts. Three-dimensional parts include parts that extend in the three dimensions of space in similar manner, including in the form of complex geometric parts (e.g., concave or convex sections, possibly including undercuts, inserts, and the like).

In some embodiments, the di-ketone polymer can be desirably incorporated into composites. In such embodiments, long fibers are solution, suspension or melt-impregnated with the di-ketone polymer to form the composite. The long fibers generally have a length of at least 10 microns ("μm"). The fibers can be glass fibers or carbon fibers. In some embodiments, the composite can form a tape or woven fabric.

Exemplary Applications

In some embodiments, the shaped article is a component of a mobile electronic device. As used herein, a "mobile electronic device" refers to an electronic device that is transported and used in various locations. A mobile electronic device can include, but is not limited to, a mobile phone, a personal digital assistant ("PDA"), a laptop computer, a tablet computer, a wearable computing device (e.g., a smart watch and smart glasses), a camera, a portable audio player, a portable radio, a global position system receiver, and portable game console.

In some embodiments, at least a portion of a component of a mobile electronic device is exposed to the external environment of the mobile electronic device (e.g., at least a portion of the component is in contact with the environment external to the mobile electronic device). For example, at least a portion of the component forms at least a portion of the external housing of the mobile electronic device. In some such embodiments, the component can be a full or partial "frame" around the periphery of the mobile electronic device, a beam in the form of a lattice work, or a combination thereof. As another example, at least a portion of the component can form at least a portion of an input device. In some such embodiments, a button of the electronic device can include the component. In some embodiments, the component can be fully enclosed by the electronic device (e.g., the component is not visible from an observation point external to the mobile electronic device).

In some embodiments, the component can be a mounting component with mounting holes or other fastening device, including but not limited to, a snap fit connector between itself and another component of the mobile electronic device, including but not limited to, a circuit board, a microphone, a speaker, a display, a battery, a cover, a housing, an electrical or electronic connector, a hinge, a radio antenna, a switch, or a switchpad. In some embodiments, the mobile electronic device can be at least a portion of an input device.

The components of the mobile electronic device can be fabricated from the di-ketone polymer compositions using methods well known in the art. For example, the mobile electronic device components can be fabricated by methods including, but not limited to, injection molding, blow molding or extrusion molding. In some embodiments, di-ketone polymer composition can be formed into pellets (e.g., having a substantially cylindrical body between two ends) by methods known in the art including, but not limited to, injection molding. In some such embodiments, mobile electronic device components can be fabricated from the pellets.

The di-ketone polymers described herein can be used in additive manufacturing (e.g. 3D printing) techniques such as fused filament fabrication (FFF) or selective laser sintering (SLS). Additive manufacturing involves the process of joining materials to make articles from 3D model data. The article is generally formed using layer-by-layer deposition. Commercially available 3D printing fabrication equipment of the FFF type include, as an example, the equipment manufactured by Stratasys, Inc. and sold under the Fortus® trademark. Examples of SLS based 3D printing equipment are available from EOS corporation such as the ones sold under the trade name EOSINT®. In such embodiments, an article can be formed by 3D printing the di-ketone polymer (or di-ketone polymer composition).

In some embodiments, the shaped articles described herein are medical devices or components of medical devices. As used herein, a "medical device" is an article, instrument, apparatus or machine that is used in the prevention, diagnosis, or treatment of illness or disease, or for detecting, measuring, restoring, correcting, or modifying the structure or function of a human or animal body.

Material selection is critical for medical devices, particularly in instances where the material is implanted in, or comes into contact with, the body. There is a continued need for medical device materials that meet the particular requirements of the medical device in its application setting (e.g. wear resistance), and also reduce or prevent undesirable interactions with the body, such as, for example, the leaching of chemicals from the medical device into the body.

The di-ketone polymers described herein may be particularly suitable for use in medical devices, for example, because of their higher purity as reflected in their reduced metals content.

Medical devices can generally include surgical devices, non-surgical devices, prosthetic devices, implants, etc.

In some embodiments, the medical device including the diketone polymers described herein is an implantable medical device (IMD). IMDs are medical devices designed to replace a missing biological structure, support a damaged biological structure, or enhance an existing biological structure in the body. Examples of IMDs include cranial implants such as craniomaxillofacial implants, spinal implants such as spinal cages and spinal disks, finger and toe implants, knee replacements, hip replacements such as acetabular caps, stents, heart valves, pacemakers, and hardware such as bone screws and plates. The medical devices may also include dental devices such as removable full and partial denture frames, crowns, bridges, artificial teeth, and implant bars.

Exemplary embodiments will now be described in the following non-limiting examples.

EXAMPLES

The following examples describe preparation of the monomer compositions and synthesis of PEKK copolymers from the monomer compositions.

Raw Materials

Solvents:

4-methyl-2-pentanone (MIBK, HPLC grade), chlorobenzene (MCB, HPLC grade), and ethanol-190 proof (USP grade), available from Aldrich.

Dimethyl sulfoxide (DMSO, HPLC grade) and N,N-dimethylformamide (DMF, HPLC grade) available from Fisher Scientific.

Ethanol-200 proof (99.85%) available from Lyondell (Equistar).

1,4-bis(4'-fluorobenzoyl)benzene was prepared by Friedel-Crafts acylation of fluorobenzene according to example 1 of U.S. Pat. No. 5,300,693, the entirety of which is incorporated herein by reference. The analysis of the product as made is detailed in Table 1 as "Starting 1,4-DFDK."

1,3-bis(4'-fluorobenzoyl)benzene available from 3B Corp, USA. The analysis of the product is detailed in Table 2 as "Starting 1,3-DFDK."

1,4-bis(4'-hydroxybenzoyl)benzene was produced by hydrolysis of 1,4-bis(4'-fluorobenzoyl)benzene following the procedure of example 1 of U.S. Pat. No. 5,250,738, the entirely of which is incorporated herein by reference. The analysis of the product is detailed in Table 3 as "Starting 1,4-BHBB (NaOH)." 1,4-bis(4'-hydroxybenzoyl)benzene was also produced by the same procedure with the exception that KOH was substituted for NaOH. The analysis of this product is detailed in Table 3 as "Starting 1,4-BHBB (KOH)."

1,3-bis(4'-hydroxybenzoyl)benzene was produced by hydrolysis of 1,3-bis(4'-fluorobenzoyl)benzene following the procedure of example 1 of U.S. Pat. No. 5,250,738. The analysis of the product is detailed in Table 4 as "Starting 1,3-BHBB (NaOH)." 1,3-bis(4'-hydroxybenzoyl)benzene was also produced by the same procedure with the exception that KOH was substituted for NaOH. The analysis of this product is detailed in Table 4 as "Starting 1,3-BHBB (KOH)."

Diphenyl sulfone (polymer grade) available from Proviron (99.8% pure).

Sodium carbonate, light soda ash, available from Solvay S.A., France, dried before use.

Potassium carbonate with a $d_{90}$<45 µm available from Armand Products, dried before use.

Lithium chloride (anhydrous powder) available from Acros.

Analysis Methods

Gas Chromatography (GC) Analysis

GC analysis was performed on an Agilent 7820A machine. 1.0 wt % solutions of the monomers in DMSO were analyzed under the following conditions:

Column: DB-5MS, 30 m×0.25 mm×0.25 µm coating
Injector temperature: 325° C.
FID detector temperature: 325° C.
Temperature profile: 100° C. for 1 min, ramp to 325° C. @ 20° C./min, hold at 325° C. for 20 min.
Injection volume: 1 µL
Split ratio: 20:1, Split flow: 20 mL/min.
Flow: 1.0 mL/min (27.596 cm/sec).

The GC purity was determined as the % area of the peak of the monomer relative to the total area of the peaks detected.

Determination of Elemental Impurities in Monomers by ICP-OES Method

For ICP-OES analysis, a clean, dry platinum crucible was placed onto an analytical balance, and the balance was zeroed. One half to three grams of monomer sample was weighed into a boat and its weight was recorded to 0.0001 g. The crucible with sample was placed in a muffle furnace (Thermo Scientific Thermolyne F6000 Programmable Furnace). The furnace was gradually heated to 525° C. and held at that temperature for 10 hours to dry ash the sample. Following ashing, the furnace was cooled down to room temperature, and the crucible was taken out of the furnace and placed in a fume hood. The ash was dissolved in diluted hydrochloric acid. The solution was transferred to a 25 mL volumetric flask, using a polyethylene pipette. The crucible was rinsed twice with approximately 5 mL of ultrapure water (R<18 MΩcm) and the washes were added to a volumetric flask to effect a quantitative transfer. Ultrapure water was added to total 25 mL in the flask. A stopper was put on the top of the flask and the contents were shaken well to mix.

ICP-OES analysis was performed using an inductively-coupled plasma emission spectrometer Perkin-Elmer Optima 8300 dual view. The spectrometer was calibrated using a set of NIST traceable multi-element mixed standards with analyte concentrations between 0.0 and 10.0 mg/L. A linear calibration curve was obtained in a range of concentrations with a correlation coefficient better than 0.9999 for each of 48 analytes. The standards were run before and after every ten samples to ensure instrument stability. The results were reported as an average of three replicates. The concentration of elemental impurities in the sample was calculated with the following equation:

$$A=(B*C)/(D)$$

where:
A=concentration of element in the sample in mg/kg (=wt.ppm)
B=element in the solution analyzed by ICP-OES in mg/L
C=volume of the solution analyzed by ICP-OES in mL
D=sample weight in grams used in the procedure.

Melting Point Analysis

The melting point was determined by differential scanning calorimetry (DSC) according to ASTM-E-74. The DSC analysis was performed on TA Instruments Q20. 5-10 mg of monomer was weighed with 5-7 mg of high purity indium (99.99% purity from LGC) and analyzed using the following temperature programs:

For 1,3-BHBB:
1: Equilibrate at 25.00° C.
2: Ramp 10.00° C./min to 205.00° C.
3: Ramp 1.00° C./min to 220.00° C.

For 1,4-BHBB:
1: Equilibrate at 25.00° C.
2: Ramp 10.00° C./min to 290.00° C.
3: Ramp 1.00° C./min to 320.00° C.

For 1,4-DFDK:
1: Equilibrate at 25.00° C.
2: Ramp 10.00° C./min to 210.00° C.
3: Ramp 1.00° C./min to 230.00° C.

For 1,3-DFDK:
1: Equilibrate at 25.00° C.
2: Ramp 10.00° C./min to 165.00° C.
3: Ramp 1.00° C./min to 190.00° C.

The melting endotherm was defined from the initial point on the curve where the endotherm deviates from the baseline to the final point on the curve where the endotherm returns to the baseline. In the melting range, the temperatures for the molten fractions at 1% and 90% of total melting endotherm were identified as the melting range of the monomer. The temperatures were corrected based on the temperature of onset of melting for indium (156.60° C.).

Determination of Inherent Viscosity

Inherent viscosity (IV) was measured following ASTM D2857 at 30° C. on 0.5 wt/vol % solutions in concentrated $H_2SO_4$ (96 wt % minimum) using a Cannon-Fenske capillary, size 200.

Determination of the Glass Transition Temperature and Melting Temperature of the PEKK Polymer The glass transition temperature Tg (at midpoint) and the melting temperature Tm were determined on the 2nd heat scan by DSC according to ASTM D3418-03, E1356-03, E793-06, E794-06 using the following parameters: A TA Instruments DSC Q20 was used with nitrogen as carrier gas (99.998% purity, 50 mL/min). Temperature and heat flow calibrations were performed using indium. The sample size was 5 to 7 mg. The weight was recorded to ±0.01 mg. The heat cycles were as follows:

1st heat cycle: 30.00° C. to 400.00° C. at 20.00° C./min, isothermal at 400.00° C. for 1 min;
1st cool cycle: 400.00° C. to 30.00° C. at 20.00° C./min, isothermal for 1 min;
2nd heat cycle: 30.00° C. to 400.00° C. at 20.00° C./min, isothermal at 400.00° C. for 1 min.

The melting temperature Tm was determined as the peak temperature of the melting endotherm on the 2nd heat scan.

Determination of the Melt Viscosity

The melt viscosity was measured using a capillary rheometer per ASTM D3835. Readings were taken after a 10 minute dwell time at 380° C. and a shear rate of 46.3 $s^{-1}$ using a die with the following characteristics: diameter=1.016 mm, length=20.32 mm, cone angle=120°.

EXAMPLES AND COMPARATIVE EXAMPLES

Comparative Example A: Recrystallization of 1,4-DFDK in Monochlorobenzene

To a 2 L flask fitted with a heating mantle, thermocouple, temperature controller, agitator and condenser, was added 100 g of 1,4-DFDK and 1800 mL (=1991 g) of monochlorobbenzene. The mixture was heated to reflux with agitation. 1,4-DFDK was in solution at reflux. While hot, the solution was filtered through a Watman 541 filter paper in a ceramic Buchner funnel that had been heated to 125° C. in the glassware oven. Once filtered, agitation was restored to the filtrate, and it was heated to reflux. Once dissolved, the heating was discontinued and the solution allowed to cool at approximately 0.3° C./min to 40° C. The heating mantle was exchanged for an ice/water bath and the slurry was further cooled to 10-15° C. with agitation and held at 10-15° C. for 1 h. The recrystallized solids were isolated by filtration in a Buchner funnel with a Whatman #4 filter paper. Air was pulled through the cake for 1 h, then the solids were transferred to an aluminum pan and vacuum oven dried at 130° C. and 27" Hg for 24 h. The solids were allowed to cool to room temperature and transferred to a tared jar to afford 92.1 g (92.1%).

Analysis of the product is shown in Table 1.

Comparative Example B: Recrystallization of 1,4-DFDK in MIBK

To a 500 ml, flask fitted with a heating mantle, thermocouple, temperature controller, agitator and condenser, was added 1,4-DFDK (20.0 g) and MIBK (305 g=244 mL). The mixture was heated, with agitation, to reflux (~115° C.). The heat was turned off to allow the solution to cool just slightly, the solution was filtered through Whatman GF/F glass fiber filter pad in a pre-heated (125° C.) ceramic Buchner funnel into a clean 500 mL 3-neck flask. The initial flask was rinsed with hot MIBK (24 g=30 mL) through the filter. The resulting filtered solution was reheated to reflux to redissolve the solids. The heating was discontinued and the solution allowed to cool with stirring at approximately 0.3° C./min to room temperature. The recrystallized solids were isolated by filtration in a Büchner funnel with a Whatman #4 filter paper. Air was pulled through the cake until no more solvent was seen dripping from the funnel. The filter cake was washed with cold MIBK and air was pulled through the pad for 20 min before being transferred to an aluminum pan and vacuum oven dried at 130° C. and 27" Hg for 64 h. The solids were allowed to cool to room temperature and transferred to a tared jar to afford 18.3 g (90%).

Analysis of the product is shown in Table 1

Example 1: Recrystallization of 1,4-DFDK in DMSO

To a 500 mL flask fitted with a heating mantle, thermocouple, temperature controller, agitator and condenser, was added 1,4-DFDK (20.0 g) and DMSO (132 g=120 mL). The mixture was heated, with agitation, to 130° C. The heat was turned off to allow the solution to cool just slightly, the solution was filtered through Whatman GF/F glass fiber filter pad in a pre-heated (125° C.) ceramic Buchner funnel into a clean 500 mL 3-neck flask. The initial flask was rinsed with hot DMSO (33 g=30 mL) through the filter. The resulting filtered solution was reheated to redissolve the solids. The heating was discontinued and the solution allowed to cool at approximately 0.3° C./min to 40° C. The heating mantle was exchanged for an ice/water bath and the slurry was further cooled to 5° C. with agitation and held at 5° C. for 1 h. The recrystallized solids were isolated by filtration in a Buchner funnel with a Whatman #4 filter paper. Air was pulled through the cake until no more solvent was seen dripping from the funnel. The solids were then transferred back to the 500 mL flask, Water and ethanol was added (250 mL of 90:10) and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 18.28 g (91%).

Analysis of the product is shown in Table 1

Example 2: Recrystallization of 1,4-DFDK in Sulfolane

To a 500 ml, flask fitted with a heating mantle, thermocouple, temperature controller, agitator and condenser, was added 1,4-DFDK (20.3 g) and sulfolane (112 g=100 mL). The mixture was heated, with agitation, to 150° C. The heat was turned off to allow the solution to cool just slightly, the solution was filtered through Whatman GF/F glass fiber filter pad in a pre-heated (125° C.) ceramic Büchner funnel into a clean 500 mL 3-neck flask. The initial flask was rinsed with hot sulfolane (38 g=30 mL) through the filter. The resulting filtered solution was reheated to redissolve the solids. The heating was discontinued and the solution allowed to cool at approximately 0.3° C./min to room temperature. The recrystallized solids were isolated by filtration in a Buchner funnel with a Whatman #4 filter paper. Air was pulled through the cake until no more solvent was seen dripping from the funnel. The solids were then transferred back to the 500 mL flask, Water and ethanol was added (250 mL of 90:10) and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 18.0 g (90%).

Analysis of the product is shown in Table 1

Example 3: Recrystallization of 1,4-DFDK in Propylene Carbonate

To a 500 ml, flask fitted with a heating mantle, thermocouple, temperature controller, agitator and condenser, was added 1,4-DFDK (37.8 g) and Propylene Carbonate (242 g=203 mL). The mixture was heated, with agitation, to 140° C. The heat was turned off to allow the solution to cool just slightly, the solution was filtered through Whatman GF/F glass fiber filter pad in a pre-heated (125° C.) ceramic Buchner funnel into a clean 500 mL 3-neck flask. The initial flask was rinsed with hot propylene carbonate (36 g=30 mL) through the filter. The resulting filtered solution was reheated to redissolve the solids. The heating was discontinued and the solution allowed to cool at approximately 0.3° C./min to room temperature. The heating mantle was replaced with an ice/water bath and the slurry was cooled to 0-5° C. and held for 1 h. The recrystallized solids were isolated by filtration in a Buchner funnel with a Whatman #4 filter paper. Air was pulled through the cake until no more solvent was seen dripping from the funnel. The wet cake was washed with cold propylene carbonate directly in the Buchner funnel and air was pulled through the pad for 20 min. The solids were transferred to an aluminum pan and vacuum oven dried at 130° C. and 27" Hg for 24 h. The solids were allowed to cool to room temperature and transferred to a tared jar to afford 36.48 g (96.5%).

Analysis of the product is shown in Table 1.

Comparative Example C: Recrystallization of 1,3-DFDK in Monochlorobenzene

In a 5 L 3-neck round-bottom flask, fitted with a stirrer, a $N_2$ inlet tube, a Claisen adapter with a thermocouple plunging in the reaction medium, and a reflux condenser were introduced 805 g of 1,3-DFDK and 4075 g (=4507 mL) monochlorobenzene (MCB. The slurry was heated up to reflux under agitation and, after all the solid had dissolved, held at reflux for 30 minutes. The mixture was then cooled down to room temperature under agitation over 12 hours, then placed in a freezer at 0° C. for at least 12 hours. The solid was filtered out on a cold Buchner funnel with P8 filter paper and the solid cake on the funnel was rinsed with 450 g of cold MCB (0° C.) then with 300 mL of methanol. The solid was dried under vacuum (P<100 Torr) at 120° C. overnight to yield 722 g of purified 1,3-DFDK (90.0% yield).

Analysis of the product is shown in Table 2.

Example 4: Recrystallization of 1,3-DFDK in DMSO

To a 500 ml, flask fitted with a heating mantle, thermocouple, temperature controller, agitator and condenser, was added 1,3-DFDK (40.4 g) and DMSO (209 g=190 mL). The mixture was heated, with agitation, to 95° C. The heat was turned off to allow the solution to cool just slightly, the solution was filtered through Whatman GF/F glass fiber filter pad in a pre-heated (125° C.) ceramic Buchner funnel into a clean 500 mL 3-neck flask. The initial flask was rinsed with hot DMSO (33 g=30 mL) through the filter. The resulting filtered solution was reheated to 95° C. and water (45 g) was added slowly to just below the saturation point. The heating was discontinued and the solution allowed to cool at approximately 0.3° C./min to room temp and held for 1 h. The recrystallized solids were isolated by filtration in a Buchner funnel with a Whatman #4 filter paper. Air was pulled through the cake until no more solvent was seen dripping from the funnel. The solids were then transferred back to the 500 mL flask, methanol was added (200 mL) and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 38.8 g (96%).

Analysis of the product is shown in Table 2.

Comparative Example D: Recrystallization of 1,4-BHBB in Ethanol/Water

To a 2 L 3-neck flask fitted with an agitator, thermocouple and reflux condenser in a heating mantle, was added 1,4-BHBB (10 g), ethanol (200 proof, 200 mL) and water (1000 mL). The mixture was heated to reflux and held for 1 hour. There was no visible difference in amount of insoluble material as compared to that at room temperature. Given the low percent solids (0.83% w/vol) and apparent lack of solubility, the experiment was discontinued.

Comparative Example E: Recrystallization of 1,4-BHBB in Ethanol (200 Proof)

To a 2 L flask fitted with a heating mantle, thermocouple, temperature controller, agitator and condenser, was added 15 g of 1,4-BHBB (Starting 1,4-BHBB (NaOH)) and ethanol (1500 mL=1184 g). The mixture was heated, with agitation, to reflux (approximately 78° C.). The heat was turned off to allow the solution to cool just below reflux, the solution was filtered through Whatman GF/F glass fiber filter pad in a pre-heated (95° C.) ceramic Büchner funnel into a clean 2 L 3-neck flask. The initial flask was rinsed with hot Ethanol (200 pf) (100 mL=79 g) through the filter. The resulting filtered solution was reheated to reflux, with agitation. Ethanol, 100 mL, was removed via distillation (strip) at atmospheric pressure to return to the original concentration. The heating was discontinued and the solution allowed to cool at approximately 0.3° C./min to 40° C. The heating mantle was exchanged for an ice/water bath and the slurry was further cooled to 0-5° C. with agitation and held at 0-5°

C. for 1 h. The recrystallized solids were isolated by filtration in a Buchner funnel with a Whatman #4 filter paper. Air was pulled through the cake until no more solvent was seen dripping from the funnel. The solids were transferred to an aluminum pan and vacuum oven dried at 120° C. and 27" Hg for 24 h. The solids were allowed to cool to room temperature and transferred to a tared jar to afford 13.2 g (88.2%).

Analysis of the product is shown in Table 3.

Comparative Example F: 1,4-BHBB Product from Hydrolysis in DMSO/Water Per Chinese Patent No. CN1974631

The procedure of Chinese Patent No. CN1976431 A—Example 1 was followed:

To a 1 L 3-neck flask, fitted with a heating mantle, thermocouple, agitator and condenser, was added 1,4-DFDK (64.4 g, 0.2 mol), KOH (56 g, 1 mol, 1.25 eq/F), $H_2O$ (300 mL), and DMSO (300 mL). The mixture was stirred for 5 minutes to fully dissolve the hydroxide before being heated to 100° C. over 30 min. The temperature was slowly increased to 105° C. at which point condensate was seen slowly dripping from the condenser. The reaction was held at this temperature for 8 h, then heating was discontinued and the mixture was allowed to cool overnight. The resulting mixture was filtered through a Whatman GF/F filter in a Buchner funnel, and the solids were washed with water (1×100 mL). The solids were transferred to an aluminum pan and vacuum oven dried at 125° C./27" Hg overnight to give 56.0 g (87%) of unreacted 1,4-DFDK. The filtrate from above was slowly acidified with Aq. HCl (37%) to pH=9.5 and stirred for 1 h. The resulting solids were isolated by filtration on a Whatman #4 filter paper in a Buchner funnel, washed with water to pH=6-7, and vacuum oven dried at 125° C./27" Hg overnight to give 0.68 g (1.08%) of a white powder. The filtrate from the pH=9.5 mixture was further acidified with Aq. HCl (37%) to pH=4 and stirred for 1 h. The resulting solids were isolated by filtration on a Whatman #4 filter paper in a Buchner funnel, washed with water to pH=6-7, and vacuum oven dried at 125° C./27" Hg overnight to give 3.30 g (5.20%) of a white powder.

Analysis of the product is shown in Table 3.

Example 5: Recrystallization of 1,4-BHBB in DMF/Ethanol

To a 5 L flask fitted with a heating mantle, thermocouple, temperature controller, agitator and condenser, was added 500 g of 1,4-BHBB (Starting 1,4-BHBB (NaOH)), DMF (1935 g=2050 mL) and ethanol (808 g=1025 mL). The mixture was heated, with agitation, to reflux (approximately 92° C.). The heat was turned off to allow the solution to cool just below reflux, the solution was filtered through Whatman GF/F glass fiber filter pad in a pre-heated (95° C.) ceramic Buchner funnel into a clean 5 L 3-neck flask. The initial flask was rinsed with hot 2:1 DMF:ethanol (89 g=100 mL) through the filter. The resulting filtered solution was reheated to reflux, with agitation, and water (850 mL, 1.7× with respect to the starting monomer weight) was added slowly over 10 min allowing any precipitate to redissolve. At the end of the water addition, the heating was discontinued and the solution allowed to cool at approximately 0.3° C./min to 40° C. The heating mantle was exchanged for an ice/water bath and the slurry was further cooled to 0-5° C. with agitation and held at 0-5° C. for 1 h. The recrystallized solids were isolated by filtration in a Buchner funnel with a Whatman #4 filter paper. Air was pulled through the cake until no more solvent was seen dripping from the funnel. The solids were then transferred back to the 5 L flask, DI water (2 L) was added and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 478 g (95.6%).

Analysis of the product is shown in Table 3.

Example 6: Recrystallization of 1,4-BHBB in DMSO/Methanol

To a 500 mL flask fitted with a heating mantle, thermocouple, temperature controller, agitator and condenser, was added 45 g of 1,4-BHBB (Starting 1,4-BHBB (NaOH)), DMSO (165 g=150 mL) and Methanol (87 g=110 mL). The mixture was heated, with agitation, to reflux (approximately 72° C.). The heat was turned off to allow the solution to cool just below reflux, the solution was filtered through Whatman GF/F glass fiber filter pad in a pre-heated (75° C.) ceramic Büchner funnel into a clean 500 mL 3-neck flask. The initial flask was rinsed with hot 2:1 DMSO:methanol (30 g=30 mL) through the filter. The resulting filtered solution was reheated to reflux, with agitation, and water (95 mL, 2.1× with respect to the starting monomer weight) was added slowly over 10 min allowing any precipitate to redissolve. At the end of the water addition, the heating was discontinued and the solution allowed to cool at approximately 0.3° C./min to 40° C. The heating mantle was exchanged for an ice/water bath and the (now) slurry was further cooled to 10-15° C. with agitation and held at 10-15° C. for 1 h. The recrystallized solids were isolated by filtration in a Buchner funnel with a Whatman #4 filter paper. Air was pulled through the cake until no more solvent was seen dripping from the funnel. The solids were then transferred back to the 500 mL flask, methanol (250 mL) was added and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 42.35 g (94.1%).

Analysis of the product is shown in Table 3.

Example 7: Recrystallization of 1,4-BHBB in DMF/Ethanol

The same procedure as Example 5 was followed, but beginning from Starting 1,4-BHBB (KOH).

Analysis of the product is shown in Table 3.

Comparative Example G: Recrystallization of 1,3-BHBB in Ethanol (200 Proof)

To a 2 L flask fitted with a heating mantle, thermocouple, temperature controller, agitator and condenser, was added 280 g of 1,3-BHBB (Starting 1,3-BHBB (KOH)), and ethanol (1000 mL=789 g). The mixture was heated, with agitation, to reflux (approximately 78° C.), and no visible insoluble materials were observed. The heating was discontinued and the solution was allowed to cool at approximately 0.3° C./min to 40° C. The heating mantle was exchanged for an ice/water bath and the slurry was further cooled to 0-5° C. with agitation and held at 0-5° C. for 1 h. The recrystallized solids were isolated by filtration in a Büchner funnel with a Whatman #4 filter paper. Air was pulled through the cake until no more solvent was seen dripping from the funnel. The solids were transferred to an aluminum pan and vacuum oven dried at 120° C. and 27" Hg for 24 h. The solids were allowed to cool to room temperature and transferred to a tared jar to afford 142.5 g (52.7%).

Analysis of the product is shown in Table 4.

Comparative Example H: Recrystallization of 1,3-BHBB in Ethanol (190 Proof)

To a 2 L flask fitted with a heating mantle, thermocouple, temperature controller, agitator and condenser, was added 180 g of 1,3-BHBB (Starting 1,3-BHBB (KOH)), and ethanol (1000 mL=789 g). The mixture was heated, with agitation, to reflux (approximately 78.8° C.). The solution was very slightly hazy at 75° C., but at reflux there were no visible insoluble materials. The heating was discontinued and the solution was allowed to cool at approximately 0.3° C./min to 40° C. The heating mantle was exchanged for an ice/water bath and the slurry was further cooled to 2-5° C. with agitation and held at 2-5° C. for 1 h. The recrystallized solids were isolated by filtration in a Buchner funnel with a Whatman #4 filter paper. Ethanol 190 pf (100 mL=79 g) chilled to 5° C. was added to the 2 L flask to transfer some remaining solids and filtered through the funnel. Air was pulled through the cake until no more solvent was seen dripping from the funnel. The solids were transferred to an aluminum pan and vacuum oven dried at 120° C. and 27" Hg for 24 h. The solids were allowed to cool to room temperature and transferred to a tared jar to afford 175.7 g (97.6%).

Analysis of the product is shown in Table 4.

Comparative Example I: 1,3-BHBB Product from Hydrolysis in DMSO/Water Per Chinese Patent No. CN1976431

The procedure of Chinese Patent No. CN1976431 A—Example 10 was followed.

Analysis of the product is shown in Table 4.

Example 8: Recrystallization of 1,3-BHBB in Ethanol/DMF

To a 5 L flask fitted with a heating mantle, thermocouple, temperature controller, agitator and condenser, was added 500 g of 1,3-BHBB (Starting 1,3-BHBB (KOH)), ethanol (1830 g=2320 mL) and DMF (293 g=310 mL). The mixture was heated, with agitation, to reflux (approximately 80° C.). The heat was turned off to allow the solution to cool just below reflux, the solution was filtered through Whatman GF/F glass fiber filter pad in a pre-heated (95° C.) ceramic Büchner funnel into a clean 5 L 3-neck flask. The initial flask was rinsed with hot 7.5:1 ethanol:DMF (81 g=100 mL) through the filter. The resulting filtered solution was reheated to reflux, with agitation, and water (300 mL, 0.6× with respect to the starting monomer weight) was added slowly over 10 min allowing any precipitate to redissolve. At the end of the water addition, the heating was discontinued and the solution allowed to cool at approximately 0.3° C./min to 40° C. The heating mantle was exchanged for an ice/water bath and the slurry was further cooled to 0-5° C. with agitation and held at 0-5° C. for 1 h. The recrystallized solids were isolated by filtration in a Buchner funnel with a Whatman #4 filter paper. Air was pulled through the cake until no more solvent was seen dripping from the funnel. The solids were then transferred back to the 5 L flask, DI water (2 L) was added and the slurry was agitated for 5 minutes and isolated by filtration in a Buchner funnel with a fresh Whatman #4 filter paper. The solids were transferred to an aluminum pan and vacuum oven dried at 130° C. and 27" Hg for 24 h. The solids were allowed to cool to room temperature and transferred to a tared jar to afford 460 g (92.1%).

Analysis of the product is shown in Table 4.

TABLE 1

Analysis of Recrystallized 1,4-DFDK

|  | Starting 1,4-DFDK | CE A | CE B | E1 | E2 | E3 |
| --- | --- | --- | --- | --- | --- | --- |
| Solvent A | — | MCB | MIBK | DMSO | Sulfolane | Propylene carbonate |
| Dielectric constant ($\varepsilon$) | — | 6 | 13 | 46 | 43 | 65 |
| Solvent B | — | None | None | None | None | None |
| Solvent C | — | — | MIBK | Water and ethanol | Water and ethanol | Propylene carbonate |
| [Monomers] in the solution solvent A + solvent B (wt %) ((wt/vol %)) | — | 4.8 (5.3) | 5.7 (4.6) | 10.8 (11.9) | 11.9 (15.0) | 12.0 (14.2) |
| Yield (%) | — | 92 | 90 | 91 | 90 | 97 |
| GC purity (area %) | 100.0 | 100.0 | 100.0 | 100.0 | 100.0 | 100.0 |
| Mp (° C.) | 220-221 | 220-221 | 219-221 | 218-220 | 215-220 | 218-220 |
| [Al] (wt.ppm) | 199.0 | 105.2 | 3.9 | 13.4 | 6.6 | 1.0 |
| [Fe] (wt.ppm) | 25.8 | 10.9 | 3.5 | 6.0 | 9.6 | 7.5 |

TABLE 1-continued

Analysis of Recrystallized 1,4-DFDK

|  | Starting 1,4-DFDK | CE A | CE B | E1 | E2 | E3 |
|---|---|---|---|---|---|---|
| [Na] (wt.ppm) | 11.3 | 8.8 | 53.0 | 1.6 | 1.9 | 1.8 |
| [K] (wt.ppm) | 3.6 | 11.9 | 1.6 | <0.8 | <1.15 | 1.8 |
| [Ca] (wt.ppm) | 25.5 | 5.1 | 4.9 | 2.2 | 2.3 | 0.8 |
| Total [metals] (wt.ppm) | 265.2 | 141.9 | 67.1 | 24 | 21.6 | 12.9 |

TABLE 2

Analysis of Recrystallized 1,3-DFDK

|  | Starting 1,3-DFDK | CE C | E4 |
|---|---|---|---|
| Solvent A | — | MCB | DMSO |
| Dielectric constant (ε) | — | 6 | 46 |
| Solvent B | — | None | water |
| Solvent C | — | MCB and methanol | methanol |
| [Monomers] in the solution solvent A + solvent B (wt %) ((wt/vol %)) | — | 16.5 (18.2) | 12.3 (13.4) |
| Yield (%) | — | 90 | 96 |
| GC purity (area %) | 99.6 | 100.0 | 100.0 |
| Mp (° C.) | 177-180 | 178-180 | 174-179 |
| [Al] (wt. ppm) | 154.2 | 49.1 | 3.1 |
| [Fe] (wt. ppm) | 4.2 | 50.8 | 3.4 |
| [Na] (wt. ppm) | 197.7 | 4.3 | 1.8 |
| [K] (wt. ppm) | 5.0 | 2.9 | 2.7 |
| [Ca] (wt. ppm) | 16.6 | 8.0 | 2.4 |
| Total [metals] (wt. ppm) | 377.7 | 115.1 | 13.4 |

TABLE 3

Analysis of Recrystallized 1,4-BHBB

|  | Starting 1,4-BHBB (NaOH) | CE D | CE E | CE F | E5 | E6 | Starting 1,4-BHBB (KOH) | E7 |
|---|---|---|---|---|---|---|---|---|
| Solvent A | — | Ethanol/water | Ethanol 200 pf | hydrolysis | DMF/ethanol | DMSO/methanol | — | DMF/ethanol |
| Dielectric Constant (ε) | — | 25/78 | 25 | — | 37/25 | 46/25 | — | 37/25 |
| Solvent B | — | — | — | — | water | water | — | water |
| Solvent C | — | — | — | — | water | methanol | — | water |
| [Monomers] in the solution solvent A + solvent B (wt %) ((wt/vol %)) | — | <0.8 (<0.8) | 1.25 (1.00) | — | 13.6 (11.0) | 13.8 (13.4) | — | 13.6 (11.0) |
| Yield (%) | — | — | 88 | — | 96 | 94 | — | 90 |
| GC purity (area %) | 99.2 | — | 100.0 | 99.4 | 100.0 | 100.0 | 99.9 | 100.0 |
| Mp (° C.) | 297-305 | — | 298-306 | 302-306 | 298-306 | 298-307 | 298-306 | 298-305 |
| [Al] (wt.ppm) | 6.6 | — | 3.2 | 2.6 | <1.2 | 2.4 | 351 | <1.5 |
| [Fe] (wt.ppm) | 61.3 | — | 2.9 | 9.2 | 3.9 | 13.0 | 65 | 5.2 |
| [Na] (wt.ppm) | 15.5 | — | 3.5 | 24.8 | 1.6 | 3.2 | 916 | 3.9 |
| [K] (wt.ppm) | 87.8 | — | 52.4 | 95.4 | <0.8 | 1.4 | 1.5 | 1.04 |
| [Ca] (wt.ppm) | 28.0 | — | 3.0 | 1.9 | 2.2 | 4.5 | 196 | 6.1 |
| Total [metals] (wt.ppm) | 199.2 | — | 65 | 133.9 | 9.7 | 24.5 | 1529.5 | 17.7 |

TABLE 4

Analysis of Recrystallized 1,3-BHBB

|  | Starting 1,3-BHBB (KOH) | CE G | CE H | CE I | Starting 1,3-BHBB (NaOH) | E8 |
| --- | --- | --- | --- | --- | --- | --- |
| Solvent A | — | Ethanol 200 pf | Ethanol 190 pf | hydrolysis | — | DMF/ethanol |
| Dielectric constant ($\varepsilon$) | — | 25 | 25 | — | — | 37/25 |
| Solvent B | — | — | — | — | — | water |
| Solvent C | — | — | — | — | — | water |
| [Monomers] in the solution solvent A + solvent B (wt %) ((wt/vol %)) | — | 26.2 (21.9) | 18.6 (15.2) | — | — | 18.5 (15.5) |
| Yield (%) | — | 53 | 98 | — | — | 92 |
| GC purity (area %) | 99.5 | 99.8 | 99.8 | 100.0 | 97.2 | 99.6 |
| Mp (° C.) | 212-215 | 212-215 | — | 210-213 | 210-213 | 213-215 |
| [Al] (wt.ppm) | <1.0 | 2.5 | 1.2 | <1.7 | 4.7 | <1.4 |
| [Fe] (wt.ppm) | 19 | 15.8 | 8.3 | 1.8 | 33.4 | 2.5 |
| [Na] (wt.ppm) | 321 | 40.0 | 17.7 | 13 | 29.9 | 1.8 |
| [K] (wt.ppm) | 1.3 | 6.1 | 2.7 | 451 | 1176 | <1.0 |
| [Ca] (wt.ppm) | 3.9 | 6.4 | 2.3 | 2.8 | 35.8 | 1.5 |
| Total [metals] (wt.ppm) | 346.2 | 70.8 | 32.2 | 470.3 | 1279.8 | 8.2 |

As shown in Tables 1, 2, 3, and 4 above, recrystallization of the bis(benzoyl)benzene monomers according to the methods described herein unexpectedly resulted in decreased metal concentrations while maintaining yields ≥90%.

For example, as shown in Table 1, the total metal concentrations for Examples E1, E2, and E3, were at least 64% lower than the lowest total metal concentration of the comparative examples (Comparative Example CE B). Similarly, at least an 88% reduction in total metal concentration was observed in Table 2 (Example E4 vs. Comparative Example CE C), at least a 62% reduction in total metal concentration was observed in Table 3 (Example E6 vs. Comparative Example CE E), and at least a 75% reduction in total metal concentration was observed in Table 4 (Example E8 vs. Comparative Example CE H). Moreover, this dramatic reduction in total metal concentration was surprisingly achieved while maintaining yields for all of Examples 1-7 of at least 90%.

In addition, for recrystallized 1,4-DFDK and 1,4-BHBB (Tables 1 and 3) it was surprisingly possible to work at concentrations above 10 wt. % of monomers, thereby increasing solvent usage efficiency.

Comparative Example J: Polymerization of 1,4-DFDK Recrystallized in MCB from Comparative Example A In a 500 mL 4-neck reaction flask fitted with a stirrer, a $N_2$ inlet tube, a Claisen adapter with a thermocouple plunging in the reaction medium, and a Dean-Stark trap with a condenser and a dry ice trap were introduced 127.83 g of diphenyl sulfone, 23.078 g of 1,3-bis(4'-hydroxybenzoyl)benzene (recrystallized from Example 7), 7.930 g of $Na_2CO_3$ and 0.078 g of $K_2CO_3$. The flask content was evacuated under vacuum and then filled with high purity nitrogen (containing less than 10 ppm $O_2$). The reaction mixture was then placed under a constant nitrogen purge (60 mL/min). The reaction mixture was heated slowly to 200° C. At 200° C., 23.647 g of 1,4-bis(4'-fluorobenzoyl)benzene (recrystallized from Comparative Example A), were added via a powder dispenser to the reaction mixture over 30 minutes. At the end of the addition, the reaction mixture was heated to 240° C. at 1° C./minute. At 240° C., a mixture of 17.124 g of 1,4-bis(4'-fluorobenzoyl)benzene (Comparative Example. A), 16.712 g of 1,4-bis(4'-hydroxybenzoyl)benzene (recrystallized from Example 5) and 5.743 g of $Na_2CO_3$ was added slowly to the reaction mixture over 30 minutes. At the end of the addition, the reaction mixture was heated to 320° C. at 1° C./minute. After 26 minutes at 320° C., 3.223 g of 1,4-bis(4'-fluorobenzoyl)benzene (Comparative Example A) were added to the reaction mixture while keeping a nitrogen purge on the reactor. After 5 minutes, 0.530 g of lithium chloride were added to the reaction mixture. 10 minutes later, another 0.403 g of 1,4-bis(4'-fluorobenzoyl)benzene (Comparative Example A) were added to the reactor and the reaction mixture was kept at temperature for 15 minutes. The reactor content was then poured from the reactor into a stainless steel pan and cooled. The solid was broken up and ground in an attrition mill through a 2 mm screen. Diphenyl sulfone and salts were extracted from the mixture with acetone and water at pH between 1 and 12. The powder was then removed from the reactor and dried at 120° C. under vacuum for 12 hours yielding 69 g of an off-white/yellow powder. The final polymer had a repeat unit (tere/iso (T/I) ratio of 71/29).

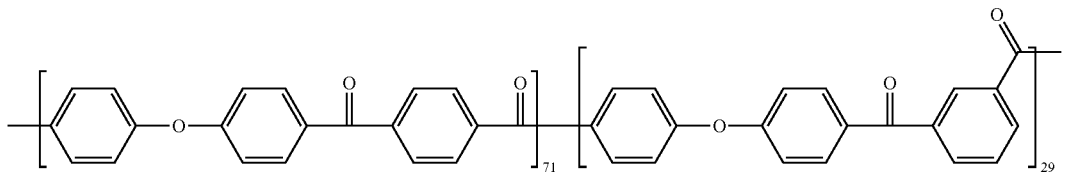

The results of the analysis of the sample are presented in Table 5.

Example 9: Polymerization of 1,4-DFDK Recrystallized in DMSO from Example 1

The same procedure as in Comparative Example I was followed but using 1,4-DFDK as recrystallized from Example 1.

The results of the analysis of the sample are presented in Table 5.

Comparative Example K: Polymerization of Non-Recrystallized 1,4-BHBB

The same procedure as in Example 9 was followed but using 1,4-DFDK as recrystallized from Example 1 and non-recrystallized 1,4-BHBB (Starting 1,4-BHBB (KOH)).

Comparative Example L: Polymerization of Non-Recrystallized 1,3-DFDK

In a 500 mL 4-neck reaction flask fitted with a stirrer, a $N_2$ inlet tube, a Claisen adapter with a thermocouple plunging in the reaction medium, and a Dean-Stark trap with a condenser and a dry ice trap were introduced 102.27 g of diphenyl sulfone, 31.833 g of 1,4-bis(4'-hydroxybenzoyl) benzene (recrystallized from Example 5), 11.023 g of $Na_2CO_3$. The flask content was evacuated under vacuum and then filled with high purity nitrogen (containing less than 10 ppm $O_2$). The reaction mixture was then placed under a constant nitrogen purge (60 mL/min). The reaction mixture was heated slowly to 180° C. At 180° C., a mixture of 14.280 g of 1,4-bis(4'-fluorobenzoyl)benzene (recrystallized from Example 1) and 18.175 of 1,3-bis(4'-fluorobenzoyl)benzene (Starting 1,3-DFDK, not recrystallized), were added via a powder dispenser to the reaction mixture over 30 minutes. At the end of the addition, the reaction mixture was heated to 310° C. at 1° C./minute. After 127 minutes at 310° C., 0.645 g of 1,4-bis(4'-fluorobenzoyl)benzene (Example 1) were added to the reaction mixture while keeping a nitrogen purge on the reactor. After 5 minutes, 0.427 g of lithium chloride were added to the reaction mixture. 10 minutes later, another 0.322 g of 1,4-bis(4'-fluorobenzoyl)benzene (Example 1) were added to the reactor and the reaction mixture was kept at temperature for 15 minutes. The reactor content was then poured from the reactor into a stainless steel pan and cooled. The solid was broken up and ground in an attrition mill through a 2 mm screen. Diphenyl sulfone and salts were extracted from the mixture with acetone and water at pH between 1 and 12. The powder was then removed from the reactor and dried at 120° C. under vacuum for 12 hours yielding 53 g of an off-white/yellow powder. The final polymer had the repeat unit (T/I ratio of 72/28):

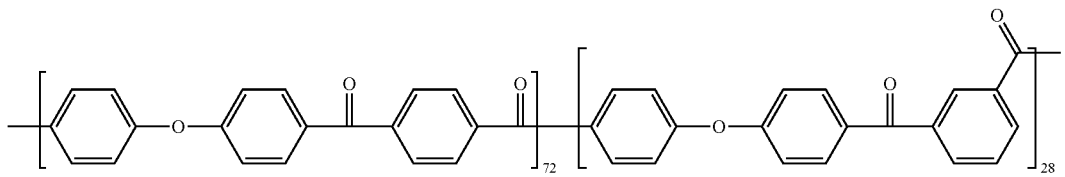

The results of the analysis of the sample are presented in Table 5.

Example 10: Polymerization of 1,3-DFDK Recrystallized in DMSO from Example 4

The same procedure as in Comparative Example L was followed but using 1,3-DFDK as recrystallized from Example 4.

The results of the analysis of the sample are presented in Table 5.

Comparative Example M: Polymerization of Non-Recrystallized 1,3-BHBB and 1,4-BHBB In a 500 mL 4-neck reaction flask fitted with a stirrer, a $N_2$ inlet tube, a Claisen adapter with a thermocouple plunging in the reaction medium, and a Dean-Stark trap with a condenser and a dry ice trap were introduced 102.27 g of diphenyl sulfone, 18.897 g of 1,3-bis(4'-hydroxybenzoyl) benzene (Starting 1,3-BHBB (NaOH)), 6.363 g of $Na_2CO_3$ and 0.024 g of $K_2CO_3$. The flask content was evacuated under vacuum and then filled with high purity nitrogen (containing less than 10 ppm $O_2$). The reaction mixture was then placed under a constant nitrogen purge (60 mL/min). The reaction mixture was heated slowly to 180° C. At 180° C., 18.918 g of 1,4-bis(4'-fluorobenzoyl)benzene (recrystallized from Example 1), were added via a powder dispenser to the reaction mixture over 30 minutes. At the end of the addition, the reaction mixture was heated to 220° C. at 1° C./minute. At 220° C., a mixture of 13.699 g of 1,4-bis(4'-fluorobenzoyl)benzene (Example 1), 13.415 g of 1,4-bis(4'-hydroxybenzoyl)benzene (Starting 1,4-BHBB (NaOH)), 4.607 g of $Na_2CO_3$ and 0.018 g $K_2CO_3$ was added slowly to the reaction mixture over 30 minutes. At the end of the addition, the reaction mixture was heated to 320° C. at 1° C./minute. After 48 minutes at 320° C., 3.223 g of 1,4-bis (4'-fluorobenzoyl)benzene (Example 1) were added to the reaction mixture while keeping a nitrogen purge on the reactor. After 5 minutes, 0.128 g of lithium chloride were added to the reaction mixture. 10 minutes later, another 0.322 g of 1,4-bis(4'-fluorobenzoyl)benzene (Example 1) were added to the reactor and the reaction mixture was kept at temperature for 15 minutes. The reactor content was then poured from the reactor into a stainless steel pan and cooled. The solid was broken up and ground in an attrition mill through a 2 mm screen. Diphenyl sulfone and salts were extracted from the mixture with acetone and water at pH between 1 and 12. The powder was then removed from the reactor and dried at 120° C. under vacuum for 12 hours yielding 52 g of an off-white/yellow powder. The final polymer had the repeat unit (T/I ratio of 71/29).

1,4-bis(4'-fluorobenzoyl)benzene (Example 1): 18.918 g
Added at 220° C.:
1,4-bis(4'-hydroxybenzoyl)benzene (Starting 1,4-BHBB (NaOH)): 13.370 g
1,4-bis(4'-fluorobenzoyl)benzene (Example 1): 13.699 g
Na$_2$CO$_3$: 4.607 g
K$_2$CO$_3$: 0.017 g
After 21 minutes at 320° C., addition of:
1,4-bis(4'-fluorobenzoyl)benzene: 3.223 g
Lithium chloride: 0.128 g
1,4-bis(4'-fluorobenzoyl)benzene: 0.322 g
Final polymer weight: 51 g

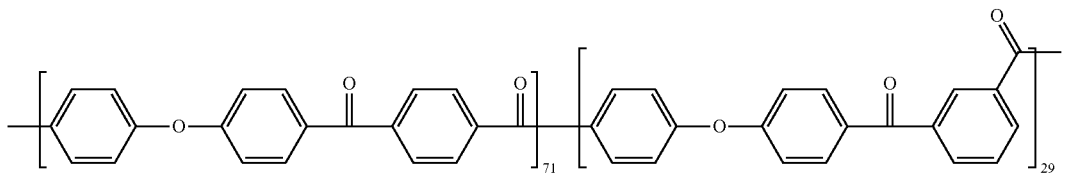

The results of the analysis of the sample are presented in table 5.

Comparative Example N: Polymerization of Non-Recrystallized 1,3-BHBB and 1,4-BHBB The same procedure as Comparative Example M was followed but with the following weights of reagents:
Diphenyl sulfone: 102.27 g
1,3-bis(4'-hydroxybenzoyl)benzene (Starting 1,3-BHBB (NaOH)): 18.707 g
Na$_2$CO$_3$: 6.363 g
K$_2$CO$_3$: 0.024 g
Added at 180° C.:

The results of the analysis of the sample are presented in table 5.

Example 11: Polymerization of Recrystallized 1,3-BHBB and 1,4-BHBB

The same procedure as Comparative Example M was followed but using 1,3-BHBB recrystallized per Example 7 and 1,4-BHBB recrystallized per Example 5.

The results of the analysis of the sample are presented in table 5.

TABLE 5

|  | CE J | E9 | CE K | CE L | E10 | CE M | CE N | E11 |
| --- | --- | --- | --- | --- | --- | --- | --- | --- |
| 1,4-DFDK | CE A | E1 | E1 | E1 | E1 | E1 | E1 | E1 |
| 1,3-DFDK | — | — | — | Starting 1,3-DFDK | E4 | — | — | — |
| 1,4-BHBB | E5 | E5 | Starting 1,4-BHBB (KOH) | E5 | E5 | Starting 1,4-BHBB (NaOH) | Starting 1,4-BHBB (NaOH) | E5 |
| 1,3-BHBB | E7 | E7 | E7 | E7 | E7 | Starting 1,3-BHBB (NaOH) | Starting 1,3-BHBB (NaOH) | E7 |
| IV (dL/g) | 1.09 | 1.00 | 1.01 | 1.18 | 1.21 | 0.98 | 1.03 | 0.95 |
| MV (Pa · s) | 1984 | 1548 | 1211 | 3692 | 4622 | 1567 | 1827 | 1182 |
| Expected MV (Pa · s) | 2100 | 1490 | 1550 | 2879 | 3179 | 1375 | 1676 | 1215 |
| ΔMV actual - exp (%) | −6 | 4 | −28 | 22 | 31 | 12 | 8 | −3 |
| Tg (° C.) | 164 | 164 | 161 | 167 | 167 | 164 | 165 | 164 |
| Tm (° C.) | 338 | 342 | 338 | 339 | 340 | 339 | 338 | 340 |

As shown in Table 5, the polymers prepared from the monomers recrystallized according the methods herein unexpectedly exhibited increased crystallinity as indicated by their higher melting temperatures.

For example, the PEKK of Example 9, which was synthesized from recrystallized 1,4-DFDK, recrystallized 1,4-BHBB, and recrystallized 1,3-BHBB exhibited a melting point of 342° C. as compared with the melting point of 338° C. observed for each of Comparative Examples J and K, which incorporated non-recrystallized 1,4-DFDK and non-recrystallized 1,4-BHBB, respectively. Similarly, the PEKK of Example 10, which was synthesized from four recrystallized monomers exhibited a melting point of 340° C. as compared with the melting point of 339° C. observed for Comparative Example L, which incorporated non-recrystallized 1,3-DFDK. Finally, the PEKK of Example 11, which was synthesized from recrystallized 1,4-DFDK, recrystallized 1,4-BHBB, and recrystallized 1,3-BHBB, exhibited a melting point of 340° C. as compared with the melting point of 338° C. and 339° C. observed for Comparative Examples M and N, respectively. Comparative Examples M and N incorporated both non-recrystallized 1,4-BHBB and non-recrystallized 1,4-BHBB.

In addition, Example 11 surprisingly exhibited increased flow vs. Comparative Examples M and N. As shown in Table 5, Example 11 exhibited a decrease of 3 Pa·s relative to the expected melt viscosity, whereas Comparative Examples M and N exhibited an increase of 12 Pa·s and 8 Pa·s, respectively, for the same measurement. The expected melt viscosity ($MV^{exp}$) was determined from the inherent viscosity as follows:

$$MV^{exp} = 1490 \, IV^{3.98}$$

where $MV^{exp}$ is in Pa·s, 1490 is a constant in (Pa·s)(g/dL)$^{3.98}$, and IV is in dL/g.

Should the disclosure of any patents, patent applications, and publications which are incorporated herein by reference conflict with the description of the present application to the extent that it may render a term unclear, the present description shall take precedence.

The invention claimed is:

1. A method for decreasing the concentration of a metal in a monomer composition comprising:
   b) recrystallizing the monomer composition in a first solvent (Solvent A), wherein:
   the first solvent (Solvent A) includes at least 10 wt. % of an aprotic solvent having a dielectric constant greater than 30, relative to the total weight of the first solvent (Solvent A), and
   the first solvent (Solvent A) includes less than 1 wt. % of inorganic salts relative to the total weight of the first solvent (Solvent A), and
   the monomer composition comprises a compound of formula:

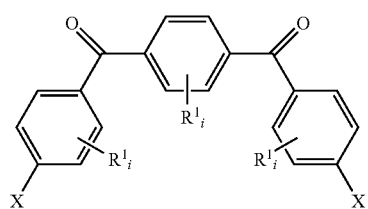

(I)

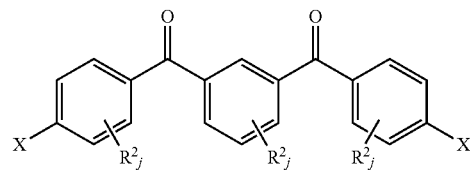

(II)

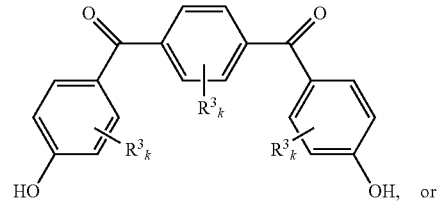

(III)

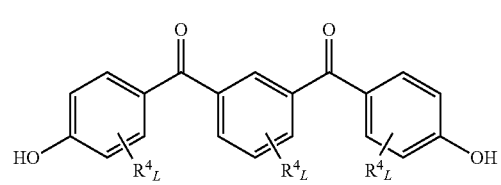

(IV)

wherein:
$R^1$, $R^2$, $R^3$ and $R^4$, at each instance, is independently selected from the group consisting of an alkyl, an alkenyl, an alkynyl, an aryl, an ether, a thioether, a carboxylic acid, an ester, an amide, an imide, an alkyl sultanate, an alkyl phosphonate, an amine, and a quaternary ammonium;

i, j, k and L, at each instance, is an independently selected integer ranging from 0 to 4;

X is a halogen; and further wherein the decreasing the concentration of a metal in a monomer composition forms a low metal monomer.

2. The method of claim 1, further comprising:
a) dissolving the monomer composition prior to the recrystallizing, wherein dissolving the monomer composition includes heating the monomer composition in the first solvent (Solvent A) to a first temperature ($T_1$) to form a monomer solution;
wherein:
the concentration of the monomer composition in the first solvent (Solvent A) ranges from about 10 to about 20 wt. % relative to the combined weight of the monomer composition and the first solvent (Solvent A); and
the first temperature ($T_1$) ranges from about 50 to about 240° C.

3. The method of claim 1, wherein recrystallizing the monomer composition comprises:
b1) optionally passing the monomer solution through a first filter;
b2) optionally distilling off a portion of the first solvent (Solvent A) at a second temperature ($T_2$),
b3) optionally adding a second solvent (Solvent B) to the monomer solution when the first solvent (Solvent A) is at a third temperature ($T_3$) to form a solvent mixture, wherein the solubility of the monomer composition in the solvent mixture is less than the solubility of the monomer composition in the first solvent (Solvent A); and
b4) optionally cooling the monomer solution to a fourth temperature ($T_4$) ranging from about −10 to about 40° C., provided that the fourth temperature ($T_4$) is greater than the melting point of the first solvent (Solvent A) and the optional second solvent (Solvent B);

provided that the method includes at least one of steps b2) and b4), and that step b1), when present, is performed before steps b2), b3), and b4), when present, wherein the first temperature ($T_1$), the second temperature ($T_2$), and the third temperature ($T_3$), identical to or different from each other, are independently selected from temperatures ranging from about 50 to about 240° C.

4. The method of claim 3, wherein the second solvent (Solvent B) is added to the monomer solution at a concentration ranging from about 5.0 to about 50 wt. % relative to the total weight of the first (solvent A) and second solvent (Solvent B).

5. The method of claim 1, further comprising:
c) recovering the monomer composition after the recrystallizing, wherein recovering the monomer composition comprises:
c1) removing the monomer composition from the monomer solution by passing the monomer solution through a second filter;
c2) optionally washing the monomer composition with a third solvent (Solvent C), wherein the third solvent (Solvent C) is identical to the first solvent (Solvent A), the second solvent (Solvent B), or a combination thereof; and
c3) drying the monomer composition.

6. The method of claim 1, wherein the inorganic salts comprise halides or oxides of Group IA, IIA, IIIa or VIII metals, or combinations thereof.

7. The method of claim 1, wherein the first solvent (Solvent A) comprises dimethyl sulfoxide (DMSO), sulfolane, propylene carbonate, N,N'-dimethylformamide (DMF), N,N'-dimethylacetamide (DMAc), N-methylpyrrolidinone (NMP), 1,3-dimethyl-2-oxo-hexahydropyrimidine (DMPU), 1,3-dimethylimidazolidin-2-one (DMEU), or combinations thereof.

8. The method of claim 3, wherein the second solvent (Solvent B) comprises water, ethanol, methanol, isopropanol, acetone, acetic acid, acetonitrile, ethyl acetate, diethyl ether, tetrahydrofuran, dipropyl ether, or combinations thereof.

9. The method of claim 1, wherein the method yields 90 wt. % or greater of the monomer composition, relative to the weight of the monomer composition before the recrystallizing.

10. The method of claim 1, wherein the low metal monomer has a total metal concentration less than 30 wt.ppm, relative to the total weight of the monomer composition.

11. A di-ketone polymer synthesized by nucleophilic substitution from monomers including bis(benzoyl)benzene monomers, wherein at least 80 mol % of the bis(benzoyl) benzene monomers are bis(benzoyl)benzene monomers recrystallized according to the method of claim 1.

12. A di-ketone polymer synthesized by nucleophilic substitution of monomers including bis(benzoyl)benzene monomers, wherein at least 80 mol % of the bis(benzoyl) benzene monomers are low metal monomers.

13. The di-ketone polymer of claim 11, wherein the metal comprises at least aluminum and/or iron, and wherein the sum of the concentrations of aluminum and iron in the di-ketone polymer is less than 30 wt.ppm, relative to the weight of the di-ketone polymer.

14. The di-ketone polymer of claim 12, wherein the metal comprises at least aluminum and/or iron, and wherein the sum of the concentrations of aluminum and iron in the di-ketone polymer is less than 30 wt.ppm, relative to the weight of the di-ketone polymer.

15. A shaped article comprising the di-ketone polymer of claim 11, wherein the shaped article is a component of an mobile electronic device or a medical device.

16. A shaped article comprising the di-ketone polymer of claim 12, wherein the shaped article is a component of an mobile electronic device or a medical device.

17. The method of claim 1, wherein X is fluorine or chlorine.

* * * * *